United States Patent [19]

Koll et al.

[11] Patent Number: 5,129,402
[45] Date of Patent: Jul. 14, 1992

[54] APPARATUS FOR COLLECTING AND/OR GROWING PROTECTED BIOLOGICAL SPECIMENS

[75] Inventors: Laurel A. Koll, Ruleville, Mich.; Charles E. Saunders, New Canaan, Conn.

[73] Assignee: Accu-Med Corporation, Pleasantville, N.Y.

[21] Appl. No.: 656,494

[22] Filed: Feb. 19, 1991

[51] Int. Cl.⁵ .............................................. A61B 10/00
[52] U.S. Cl. .................................................. 128/759
[58] Field of Search ................ 128/749, 756, 757, 759

[56] References Cited

U.S. PATENT DOCUMENTS

| | | | |
|---|---|---|---|
| 2,847,000 | 8/1958 | Nieburgs | 128/2 |
| 3,394,699 | 7/1968 | Koett | 128/2 |
| 3,513,830 | 5/1970 | Kalayjian | 128/2 |
| 3,674,007 | 7/1972 | Freis | 128/2 |
| 3,776,219 | 12/1973 | Brown | 128/2 |
| 3,800,781 | 4/1974 | Zalucki | 128/2 |
| 3,995,618 | 12/1976 | Kingsley et al. | 128/2 B |
| 4,023,559 | 5/1977 | Gaskell | 128/2 W |
| 4,136,680 | 1/1979 | Southworth | 128/213 |
| 4,157,709 | 6/1979 | Schuster et al. | 120/759 |
| 4,184,483 | 1/1980 | Greenspan | 128/759 |
| 4,223,093 | 9/1980 | Newman et al. | 435/295 |
| 4,235,244 | 11/1980 | Abele et al. | 128/749 |
| 4,318,414 | 3/1982 | Schuster et al. | 128/759 |
| 4,457,313 | 7/1984 | Alter | 128/759 |
| 4,485,824 | 12/1984 | Koll | 128/756 |
| 4,586,604 | 5/1986 | Alter | 206/210 |
| 4,653,510 | 3/1987 | Koll | 128/756 |
| 4,877,037 | 10/1989 | Ko et al. | 128/756 |

Primary Examiner—Max Hindenburg
Attorney, Agent, or Firm—Nixon & Vanderhye

[57] ABSTRACT

A specimen collector includes an elongated outer hollow tube having a forward end and a rearward end, and an inner elongated rod having a forward and rearward end portions slidably mounted within the outer tube. A specimen collector swab is mounted to the forward end of the inner rod, while a rearward extension including a gripping means is attached to the rearward end of the inner rod in order to effect sliding movement of the inner rod relative to the outer tube.

A coaxial space between the inner rod and the outer tube is divided by a plurality of axially spaced seals. The first or forward seal is mounted to the forward end of the outer cylindrical tube and is openable to permit the specimen collector or swab to pass through the seal when the inner rod is moved forward relative to the outer tube. This first or forward seal has a rounded or dome-like forward portion and a rearward cylindrical portion which terminates in a rearward end. The rearward end incorporates means for attaching the forward seal within the forward end of the outer tube. The forward domed portion of the seal is divided into a plurality of substantially identical petal-like appendages, each of which is pivotably movable between open and closed positions. A second seal is mounted at the forward end of the inner rod, just behind the specimen collector swab. A third seal is fixedly mounted to the inner surface of the outer tube and includes a centrally located aperture to permit the inner rod to move slidably therethrough.

34 Claims, 3 Drawing Sheets

APPARATUS FOR COLLECTING AND/OR GROWING PROTECTED BIOLOGICAL SPECIMENS

BACKGROUND AND SUMMARY OF THE INVENTION

This invention is generally directed to an apparatus for collecting and/or growing protected biological specimens. It is particularly directed to a novel structure for obtaining, transporting and/or growing biological specimens which are completely protected from contamination at all times after initial capture.

The problem of protecting a biological specimen from contamination during and after its initial capture is an old one. That is, it is well known that unless special precautions are taken, a given biological specimen may inadvertently become contaminated during the collection process and/or during transfer of the collected specimen to a growing medium or the like. Once thus contaminated, the worth of the specimen for diagnostic or research purposes may be greatly reduced or even eliminated.

Deep cavity cultures as well as shallow cavity cultures (e.g. abscesses, surgical incisions, etc.) are an everyday necessity in medicine, both human and veterinary. The results of these cultures must be accurate in order for a doctor to be certain of the condition and of the type of treatment necessary, if any. The uses vary from remedial to lifesaving, to status, as in the case of many veterinary uses. One such veterinary use would be in determining the bacterial count and type in the uterus of an equine mare prior to breeding.

Since the specimens are obtained in non-sterile environments, for the most part, it is imperative that the specimen be protected from contamination from the outer extremities of these cavities, as well as from air, which, for example, generally contains bacteria. Any contamination with bacteria from the air or outer extremities of the cavity would provide false or misleading diagnosis of the condition sought.

Certain prior attempts have been made to minimize contamination by inserting a device including two tubes, one within the other, to the desired depth in the cavity. Upon insertion, the inner tube, or rod is extended past the end of the outer tube, and a cotton swab contained on the end of the inner tube is saturated with mucosa from the walls of the cavity at the desired point. Upon saturation, the inner tube is withdrawn into the outer tube and then both withdrawn as a unit to the outside air.

For the bacteria contained in the mucosa on the swab to survive and grow, they must be placed in a growth environment medium, most generally in the form of a sterile liquid or gel. This is generally in a test tube like container. The procedure is to remove the mucosa saturated swab from the outer tube and place it in the tube of growth medium, cutting or breaking off the tube and placing a stopper in the tube. It is then transported to the lab where the growing culture is identified by laboratory techniques.

Typical prior art approaches to this problem are illustrated in the following prior issued U.S. patents:

U.S. Pat. No. 3,513,830—Kalayjian (1970)
U.S. Pat. No. 4,136,680—Southworth (1979)
U.S. Pat. No. 4,235,244—Abele et al. (1980)
U.S. Pat. No. 3,394,699—Koett (1968)
U.S. Pat. No. 3,674,007—Freis (1972)
U.S. Pat. No. 3,800,781—Zaluchi (1974)
U.S. Pat. No. 3,995,618—Kingsley et al. (1976)
U.S. Pat. No. 4,023,559—Gaskell (1977)
U.S. Pat. No. 4,157,709—Schuster (1979)
U.S. Pat. No. 4,184,483—Greenspan (1980)
U.S. Pat. No. 4,223,093—Newman et al. (1980)

Kalayjian and Abele et al. are both typical of prior art approaches where a biological specimen collecting swab attached to the end of an elongated rod is protected within a outer hollow tube structure temporarily sealed with a cap-like seal at its distal end. In use, the sealed distal end of the rod and tube assembly is projected into an internal body organ or the like where the desired biological sample naturally resides. Thereafter, the rod is extended to displace the seal at the distal end of the tube and to expose the swab at the desired biological site. After the specimen has been collected on the swab, it is then withdrawn into the outer protective tube and the entire assembly is withdrawn from the body organ or the like. Later, the rod with the biological swab is transferred from the protective tube to a culture growth medium or the like in another structure. As will be appreciated, many types of bacteria can be seriously contaminated, and/or killed, by even brief exposure to oxygen in the air, or other gaseous, liquid or solid contaminants that may be encountered whenever the swab is not in a completely protected environment.

Southworth provides an apparatus which attempts to more completely protect the biological specimen. For example, the distal end of the outer hollow protective tube includes a hinged cap assembly that is designed to provide some protection both before and after the swab is used for collecting a biological specimen. Furthermore, provisions are made for withdrawing the collected specimen directly into an enlarged anterior chamber where a culture growth medium or the like is provided. However, the hinged protective cap structure in Southworth is not believed to provide true isolation or absolute protection from the ambient environment and, in any event, the overall multi-part apparatus appears to be relatively complex and expensive.

The remaining patents referenced above are typical of other types of instruments for obtaining biological specimen. However, none of them are believed to describe a structure which may be used for collecting the biological specimen and thereafter transporting it to a desired culture growth medium or the like in a completely protected environment, or in an anaerobic state.

To a large degree, problems noted above have been solved by the inventions described in commonly assigned prior U.S. Pat. Nos. 4,653,510 and 4,485,824, which disclose specimen collecting devices incorporating relatively movable inner rod and outer tubular elements which enable biological specimens to be collected at the natural biological site and thereafter maintained in a completely protected environment at all times while being transported away from the natural biological site and into the presence of desired biological growth materials, transport materials, release agents, etc.

There are instances, however, where the specimen collectors described in the above identified commonly assigned patents are not wholly satisfactory. For example, where a doctor is trying to touch a small lesion (less than ¼ inch in diameter) or a puss pocket in a wound, the front seal mounted forward of the swab (for sealing the inner rod and outer tube when the swab attached to the inner rod is fully retracted into the outer tube) may prevent him from obtaining a sample. Similarly, it may be difficult to touch areas in the back of the throat or trachea because of the presence of the front seal, and to twist or bend the front seal away from the area to be touched, can cause patient discomfort.

In other instances where the swab is surrounded by body fluids or tissues on which there is a large surface area, the specimen collectors as described in the above patents do not present this problem. However, in those special situations mentioned above, the front seal located forward of the swab does in fact limit the specimen sampling.

This present invention relates to a novel and unique specimen collector which also utilizes a swab connected to an inner rod movable out of and into an outer tubular element. In this invention, the forward seal is attached to the outer tube of the collector which allows the inner rod and attached swab to pierce this unique seal design for specimen collecting, and then to be withdrawn back into a protected environment within the outer tube without contamination.

Thus, in one exemplary embodiment of the invention, a specimen collector includes an elongated outer hollow cylindrical tubular member having a forward end and a rearward end. An inner elongated rod having a forward and rearward end portions is slidably mounted within the outer tube. A specimen collector swab is mounted to the forward end of the inner rod, while a rearward extension including a gripping means is attached to the rearward end of the inner rod in order to effect sliding movement of the inner rod relative to the outer tube.

A coaxial space between the inner rod and the outer tube is divided axially by a plurality of seals. As already noted, a first or forward seal is provided at the forward end of the outer tube. A second seal is mounted at the forward end of the inner rod, just behind the specimen collector swab. A third seal is fixedly mounted to the inner surface of the outer tube and includes a centrally located aperture to permit the inner rod to move slidably therethrough. A fourth seal, similar to the third seal, may be mounted some distance behind the third seal and may also be fixed to the inner surface of the outer tube for preventing entry of contaminants that may be present on the inner rod from passing the third seal. If desired, a guide may be fixed to the rearward end of the inner rod just ahead of the rearward extension and finer loop. This guide has an outer diameter slightly less than the inner diameter of the outer tube so as to guide the rearward end of the inner rod in substantially straight line movement within the outer tube.

It is a significant feature of this invention that the first or forward seal mounted to the forward end of the outer cylindrical tube is openable to permit the specimen collector or swab to pass through the seal when the inner rod is moved forward relative to the outer tube. This first or forward seal has a rounded or dome-like forward portion and a rearward cylindrical portion which terminates in a rearward end. The rearward end incorporates means for attaching the forward seal within the forward end of the outer tube. The arrangement here is such that, when the swab element is positioned adjacent the first or forward seal, the latter cannot be separated from the outer tube.

The forward domed portion of the seal, in an exemplary embodiment, is divided into four substantially identical petal-like appendages, each of which is pivotably movable between open and closed positions and which originate in a relatively thickened base area where the forward domed portion joins with the relatively thinner rearward cylindrical portion. This thickened base portion is shaped to form a annular corner surface where it joins with an interior surface of each of the petal-like appendages.

Upon forward motion of the inner rod, the specimen collector or swab will first engage the above described annular corner or edge surfaces on the interior of the petal-like appendages to thereby push the latter to an open position. This unique construction of the seal, as further defined hereinbelow, insures that the specimen collector will not come into contact with any surfaces of the petal-like appendages which are otherwise exposed when the forward seal is in the open position.

The coaxial space between the forward seal and the second flexible seal creates a first forward chamber extending between the two seals. Similarly, the coaxial space between the second and third seals creates a second chamber, and because the second seal moves axially with the inner rod, the volume of the two chambers varies upon extension and/or retraction of the inner rod relative to the outer tubular member as in my previously described patents. A more detailed description of the seals and the function of the associated chambers will be provided hereinbelow.

It is a significant advantage of this invention that the specimen collector as described may be combined with a non-foamed, molded and sintered porous plastic swab element (additional details are provided further herein) which has been proven to be very effective in terms of its ability to pick up and release fluids quickly and uniformly.

Thus, in accordance with an exemplary embodiment of the invention, there is provided, broadly, a specimen collector which comprises an outer tubular member having a forward end including a forward edge, and a rearward end; an inner rod slidably received within the outer tubular member and having a swab element attached to a forward end thereof; a first seal mounted to the forward end of the outer tubular member comprising a forward portion including a plurality of appendages movable between closed and open positions, and a rearward portion received within the forward end of the outer tubular member such that the forward edge of the outer tubular member provides a fulcrum for movement of the appendages from the closed to the open position; and a second seal mounted on the inner rod behind the swab element.

In another aspect, the invention provides a specimen collector device comprising an outer tubular member having a forward edge and a rearward edge; an inner rod slidably received within the outer tubular member and having a swab element attached to a forward end thereof, the inner rod movable within the outer tubular rod between a retracted position where the swab element is located within the outer tubular member and an extended position where the swab element is located outside the tubular member; and at least one seal fixed to the outer tubular member adjacent the forward edge, the seal having a forward end portion including a plurality of pivotable appendages extending beyond the forward edge and movable between closed and open positions, and a rearward portion received within the outer tubular member rearward of the forward edge, the first seal having an interior thickened area between the forward and rearward portions, engageable by the swab element upon movement to its extended position.

In still another respect, the invention relates to a specimen collector comprising an outer tubular member having a forward end including a forward edge, and a rearward end; an inner rod slidably received within the outer tubular member and having a non-foamed, molded porous plastic swab element attached to a forward end thereof, and a finger grip attached to a rearward end thereof to thereby enable the swab element to be moved out of and back into the outer tubular member between extended and retracted positions; a first seal mounted to the forward end of the outer tubular member comprising a forward portion including a plurality of appendages movable between closed and open positions, and a rearward portion received within the forward end of the outer tubular member such that the forward edge of the outer tubular member provides a fulcrum for movement of the appendages from the closed to the open position; a second seal mounted on the inner rod behind the swab element; and a third seal mounted within and fixed to the outer tubular member rearwardly of the second seal and having an aperture therein to permit the inner rod to slide therethrough.

Additional objects and advantages of the subject invention will become apparent from the detailed description which follows.

DETAILED DESCRIPTION OF THE DRAWINGS

Figure 1:
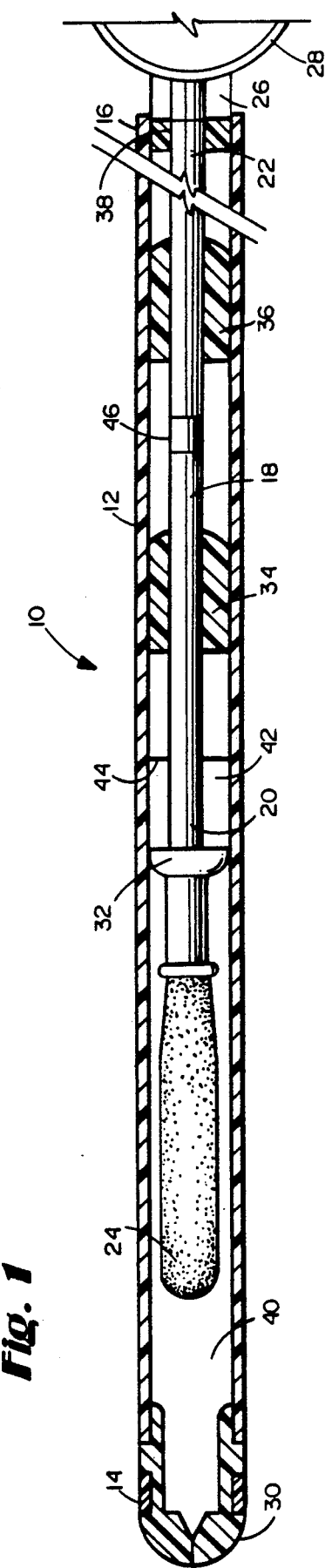
FIG. 1 is a partial cross sectional view of a specimen collector in accordance with this invention.

With reference to FIG. 1, an exemplary embodiment of the specimen collector is shown at 10, and includes an elongated outer hollow cylindrical or tubular member 12 having a forward end portion 14 and a rearward portion 16. The collector also includes an inner elongated rod 18 having forward end portion 20 and a rearward end portion 22. A specimen collector swab 24 is mounted to the forward end portion 20 of the rod 18 as will be explained in further detail below.

The rearward end portion 22 of the rod 18 is provided with a rearward extension 26 which terminates at a finger gripping loop 28 for facilitating sliding movement of the inner rod 18 relative to the outer tubular member 12. It will be appreciated, however, that any suitable gripping arrangement may be incorporated in, or attached to, the rearward end 22 of the rod 18.

As may be observed from FIG. 1, the outer diameter of the inner rod 18 is significantly less than the inner diameter of the outer tubular member 12 so that a coaxial space is created therebetween, in which various materials may be contained. The coaxial space is axially divided by a plurality of seals. Specifically, a forward seal 30 is mounted within the forward end 14 of tubular member 12. A second flex seal 32 is mounted at the forward end 20 of rod 18 just behind the specimen collector 24. A third seal 34 is fixedly secured to the inner surface of the outer tubular member 12 and includes a centrally located aperture to permit the inner rod 18 to move slidably within the seal. A fourth seal 36 may be mounted some distance behind the seal 34 and is otherwise similarly constructed and fixed within the outer tubular member 12. This fourth seal serves to prevent contamination which might be present on rod 18 from passing the third seal 34 and entering the chamber 42.

A guide 38 may be fixed to the inner rod 18 and may have an outer diameter just slightly less than the inner diameter of the outer cylinder 12 to guide the inner rod 18 in substantially linear motion during extension and retraction of the inner rod 18 relative to the outer tubular member 12.

The first seal 30 serves to seal the forward end of the outer tubular member 12 but is openable to permit the specimen collector 24 to pass through the seal when the inner rod 18 is moved forward relative to the outer tubular member 12. The second flexible seal 32 mounted at the forward end 20 of the rod 18 and behind the specimen collector 24 combines with the first seal 30 to form a first forward chamber 40 extending between the seals 30 and 32. Similarly, the seal 32 and the seal 34 create a second rearward chamber 42. Since the rod 18 is movable axially with respect to the outer tubular member 12, it will be appreciated that the chambers 40 and 42 have variable volumes which will change as a function of the sliding action of the rod 18. On the other hand, since the seals 34 and 36 are fixed to the outer cylinder 12, the volumetric space therebetween will remain constant.

A first indicator line 44 may be circumscribed about a score line formed in the periphery of the outer tubular member 12 in an area forward of the seal 34 for a purpose to be described further hereinbelow. Similarly, an indicator 46 may be applied in any suitable manner to the rod 18 in an area of the rod which is generally confined between the seals 34 and 36 when the rod 18 is in its retracted position, as will also be described in further detail below.

The second or rearward chamber 42 may be filled initially with a culture growth medium, a culture transport medium, a biological release agent, etc. The remainder of the chamber 42 and the entirety of chamber 40 are normally filled with a non-contaminated, non-reactive gas or liquid.

Figure 3:
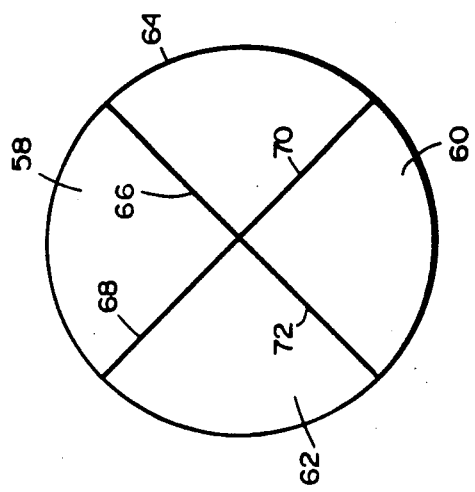
FIG. 3 is a front end view of the specimen collector illustrated in FIG. 1.
Figure 2:
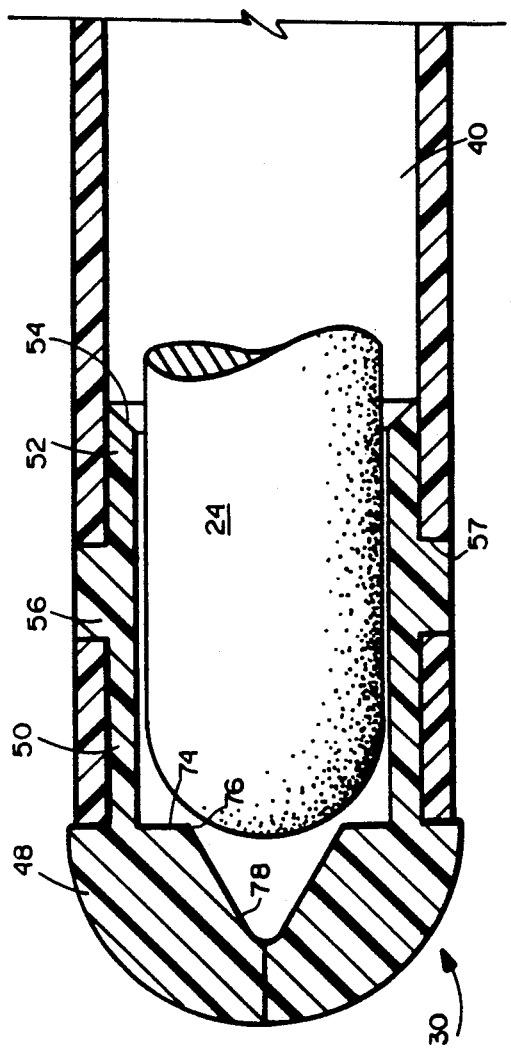
FIG. 2 is an enlarged cross sectional view of the forward portion of the specimen collector illustrated in FIG. 1.

With reference now especially to FIGS. 2 and 3, it may be seen that the forward seal 30 has a rounded or dome-like forward portion 48 and a rearward cylindrical portion 50 which terminates in a rearward end 52 at a tapered edge 54. A plurality of protrusions 56 are molded in, and spaced annularly about, the rearward portion 40, and are designed snugly fit within corresponding apertures 57 formed within the outer tubular member 12. It will be appreciated that the outermost radial dimension of the swab element is less than the inner diameter of the rearward cylindrical portion 50. However, because the radial clearance between the swab 24 and the cylindrical portion 50 is less than the radial thickness of the protrusions 56, the forward seal 30 will be retained securely within the outer tubular member 12 and will not become dislodged during use when at least a portion of the swab element lies radially adjacent the seal. Other suitable means for securing the forward seal 30 may also be used.

Figure 6:
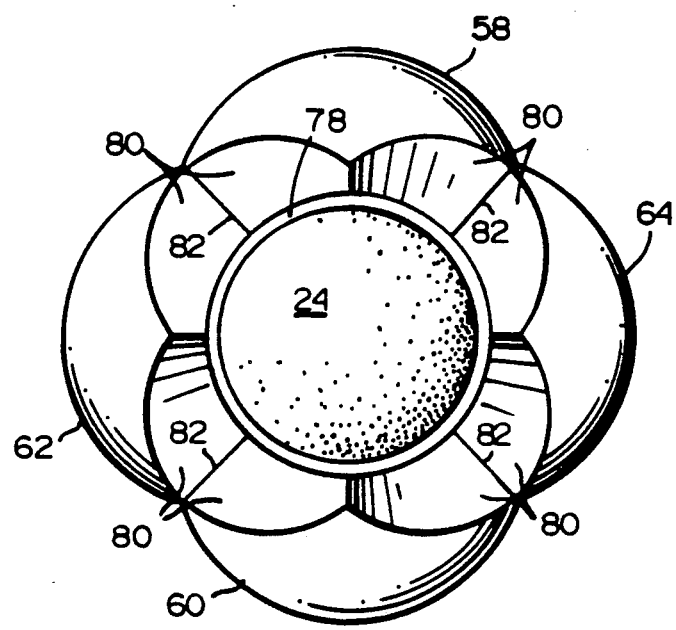
FIG. 6 is a front end view of the forward seal as illustrated in FIG. 3 but in a fully open position.

As best seen in FIG. 3, the forward domed portion 48 of the seal 30 is divided into four substantially identical petal-like appendages 58, 60, 62 and 64. Each of the appendages has a pair of sealing surfaces 80 diverting from an edge 82 (see FIG. 6) which engage similar surfaces on adjacent appendages so that four intersecting sealing lines 66, 68, 70 and 72 are established when the seal is in its closed or sealing condition. It should be understood, however, that as few as two or more than four appendages may be employed.

With reference again to FIG. 2, the interior portion of the dome-like forward portion 48, and specifically the interior surfaces of the petal-like appendages 58, 60, 62 and 64 include a relatively thickened base area 74 where they join to the relatively thinner rearward cylindrical portion 50. This thickened portion 74 forms a corner surface or edge 76 where it joins with an angled surface 78 on the interior of each of the appendages.

Figure 4:
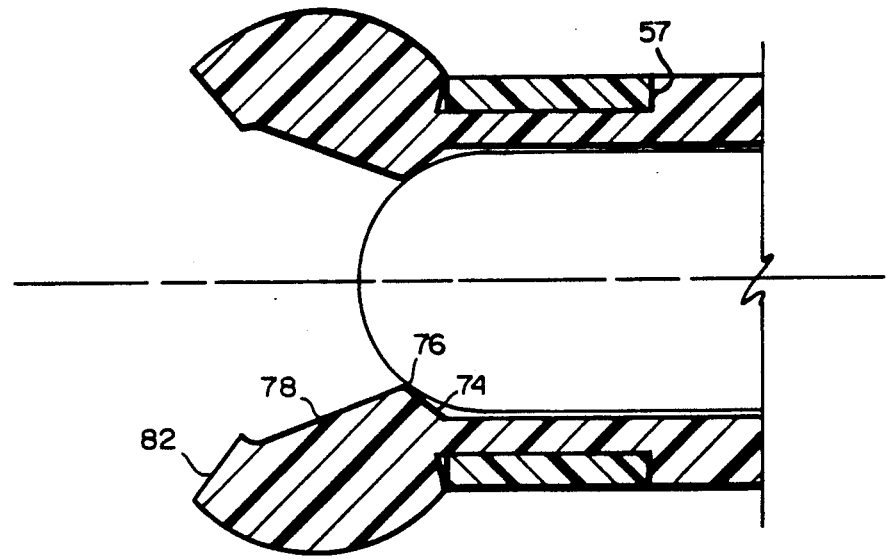
FIGS. 4 and 5 are partial cross sectional side views similar to that illustrated in FIG. 2, and showing the manner in which the forward seal is opened by the specimen collector or swab.
Figure 5:
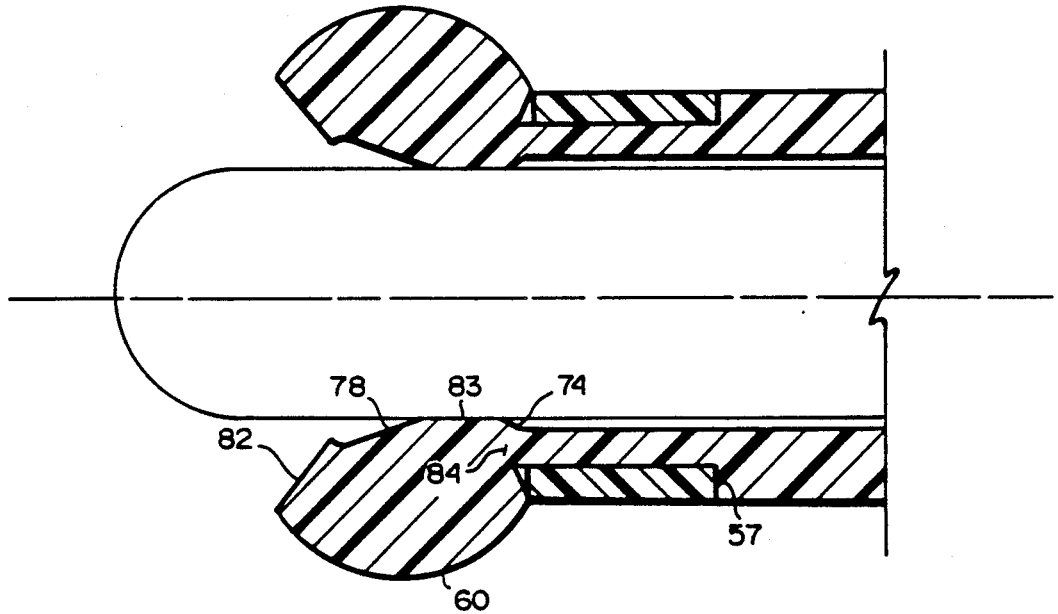

With reference now to FIGS. 4 and 5, upon forward motion of the inner rod 18, the specimen collector or swab 24 will first engage the corner or edge 76 as it pushes the petal-like appendages 58, 60, 62 and 64 to an open position, by reason of a flexing or hinging action of the petal-like appendages where the latter join with the cylindrical portion 50. As a result of the construction, the petal-like appendages pivot about the forward edge of the outer tubular member 12 which acts as a fulcrum. This action causes a stretch of the forward seal in the area 84 where the thickened portion joins with the cylindrical inner or rearward portion 50 and which insures an elastic type retraction of the petal-like appendages upon retraction of the rod 18 and specimen collector 24 into the outer tubular member 12. This stretching or tension force can be varied by design of the forward wall portion of the outer tubular member 12, or by pre-loading the tension by varying the distance between the locking holes 57 and the forward end of the tubular element 12. As shown in FIG. 5, and as a result of the flexible material of which the forward seal 48 is constructed, the corners 76 will flatten somewhat and merge with portions of the surfaces 78 to create flattened engagement surfaces 83. It should be understood, however, that the degree of flattening must be controlled to insure that the remaining portion of surfaces 78, surfaces 80 and edges 82 do not contact the swab or collector 24 when the forward seal is opened during extension of the collector, and further insures that the appendages will not collapse onto the collector during retraction.

In use, and after the forward end of the collector 10 shown in FIG. 1 is inserted to the desired site of a biological specimen (for example, deep within an internal organ of a human or animal), the inner rod 18 is moved forwardly to a position as shown in FIG. 5 so as to expose the specimen collector or swab 24 and to unseal the forward end of the tubular member 12 and forward chamber 40. By thus moving the rod 18 forwardly, the volume of the rearward chamber 42 increases while the volume of forward chamber 40 decreases as the latter is unsealed so as to permit the capture of a biological specimen. The disk-like seal 32 has a peripheral flap-like skirt that may be chosen to have a desired degree of flexibility or stiffness by choosing its composition and thickness accordingly.

In some embodiments, it may be desirable to make the periphery of the seal 32 quite flexible such that part of the filling from chamber 40 will actually flex the periphery of the seal 32 and pass it to the chamber 42 when the rod 18 is moved forwardly, thus relieving a relatively lower pressure in chamber 42 caused by movement of the rod 18. On the other hand, it may be desired to make the seal 32 somewhat stiffer in its periphery so as to create a relatively lower pressure in chamber 42 as the rod 18 is extended forwardly. In this way, when the rod 18 is then again moved rearwardly into the outer cylinder 12, a relatively lower pressure area may be created in the forward chamber 40 so as to draw additional volumes of biological specimen into the chamber.

Upon retraction of the rod 18 into the outer tubular member 12, the forward seal 30 will automatically close and seal the entry to the forward chamber 40. As the rod 18 continues to move rearwardly, the flexible, peripheral skirt of seal 32 will invert so as to provide a sliding sealing contact with the inside walls of the outer cylinder 12. At the same time, a reduction of the volume of rearward chamber 42 caused by the rearward movement of the rod 18 produces a pressure buildup until the periphery of the disk-like seal 32 is again flexed or inverted so as to permit the prefilled material in chamber 42 to pass into the chamber 40 and into direct contact with the biological specimen.

In the above described manner, the biological specimen is captured at its natural site and is transferred to a desired growth medium or the like wholly within the protected coaxial sealed chambers 40 and 42. At the same time, the unique arrangement and construction of the forward seal 30 prevents any contamination of the specimen as it is withdrawn into the chamber 40.

In order to facilitate shipment to a laboratory for analysis and/or storage, the collector may be broken at the line 44 to thereby create a relatively small specimen container, sealed at one end by the first seal 30 and at the other end by the second seal 32. The user will know generally when this may be done, as indicated by the presence of indicator 46 between the third and fourth seals 34, 36, respectively.

The forward, intermediate and rear seals 30, 32, 34 and 36, respectively, are preferably made of a medical grade silicone elastomer or similar suitable material. The guide 38 may be constructed of the same plastic material as rod 18, extension 26 and loop 28.

The specimen collector swab 24 is preferably constructed of a non-foamed, molded porous plastic material of the type manufactured and sold by Porex Technologies Corp., of 7380 Bohannon Rd., Fairburn, Ga. or Chromex Corp. of 19 Clay St., Brooklyn, N.Y. This material is initially in powder form and is compressed, molded and sintered to provide a porous plastic characterized by particles or globules of plastic fused together to provide a tortuous interstitial arrangement which provides excellent pick-up and release characteristics. The presently preferred material for the swab element 24 is a polymer such as high density polyethylene, ultra-high molecular weight polyethylene, polypropylene, polyvinyledene fluoride, ethylene-vinyl acetate, styrene-acrylonitrile polytetrafluoroethylene, or silicone rubber, etc. Pore sizes may range from about 10 to about 2,000 microns with a density of 35% to 60% void volume. The hardness of the chosen materials may range from soft through resilient to rigid, and the materials are chemically inert to most chemicals and solvents. Temperature resistance ranges from $-100°$ to $350°$ F. Hydrophylic treatment may be utilized in the manufacture of the swabs to enhance the acceptance of aqueous products. Conversely, hydrophobic swabs may be used to absorb only non-aqueous products, a feature that was heretofore unobtainable with conventional swabs or applicators. The materials are naturally white in color but can easily be colored or shaded to exact specifications.

The swab 24 may be molded in precision molds to exacting shape and size with very close tolerances.

The swab element 24 may be solid, or provided with an internal bore, and may be attached to the rod 18 preferably by ultrasonic welding or other suitable welding methods, or by compression fit or other suitable mechanical means. Alternatively, the swab element 24 and elongated rod 18 or stem may be molded as a single, solid unit.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A specimen collector device comprising:
   an outer tubular member having a forward end including a forward edge, and a rearward end;
   an inner rod slidably received within said outer tubular member and having a swab element attached to a forward end thereof for movement between retracted and extended positions;
   a first seal mounted to said forward end of said outer tubular member comprising a forward portion including a plurality of appendages movable between closed and open positions, and a rearward portion received within the forward end of the outer tubular member such that said forward edge of said outer tubular member provides a fulcrum for movement of said appendages from said closed to said open position; and
   a second seal mounted on said inner rod behind said swab element.

2. The specimen collector of claim 1 wherein said forward portion of said first seal is joined to said rearward portion at a thickened base portion which provides an abutment surface for engagement with the swab element as it moves from said retracted to said extended position.

3. The specimen collector of claim 2 wherein said abutment surface prevents contact of said swab element with any remaining portions of said appendages during extension or retraction of said swab element.

4. The specimen collector of claim 1 and including a third seal mounted within and fixed to said outer tubular member rearwardly of said second seal and having an aperture therein to permit said inner rod to slide therethrough.

5. The specimen collector of claim 4 and including a fourth seal mounted within and fixed to said outer tubular member rearward of said third seal.

6. The specimen collector of claim 5 and including a guiding element attached to a rearward portion of said inner rod.

7. The specimen collector of claim 4 and including first and second variable volume chambers between said first and second, and second and third seals, respectively, said second seal permitting passage of fluid between said first and second chambers.

8. The specimen collector of claim 7 wherein said second chamber is prefilled with any one of a culture growth medium, culture transfer medium or biological release agent.

9. The specimen collector or claim 1 wherein said plurality of appendages comprises four substantially identical petal-like elements.

10. The specimen collector of claim 1 wherein said first seal is constructed of a silicone elastomer.

11. The specimen collector of claim 1, wherein said swab element comprises a non-foamed, molded porous plastic material.

12. The specimen collector of claim 1 and further including gripping means located at a rearward end of said inner rod.

13. A specimen collector device comprising an outer tubular member having a forward edge and a rearward edge;
   an inner rod slidably received within said outer tubular member and having a swab element attached to a forward end thereof, said inner rod movable within said outer tubular rod between a retracted position where said swab element is located within said outer tubular member and an extended position where said swab element is located outside said tubular member; and
   at least one seal fixed to said outer tubular member adjacent said forward edge, said seal having a forward end portion including a plurality of pivotable appendages extending beyond said forward edge and movable between closed and open positions, and a rearward portion received within said outer tubular member rearward of said forward edge, said first seal having an interior thickened area between said forward and rearward portions, engageable by said swab element to open said seal upon movement of said swab element to its extended position.

14. The specimen collector of claim 13 wherein said thickened area includes an annular edge which flattens to an annular surface upon engagement with said swab element.

15. The specimen collector of claim 14 wherein said annular edge lies adjacent said forward edge.

16. The specimen collector of claim 15 wherein said forward edge provides a fulcrum for said appendages during movement from said closed to said open positions, creating tension in said rearward portion which tends to move said appendages to said closed position upon retraction of said inner rod.

17. The specimen collector of claim 13 and further including a second seal mounted on said inner rod behind said swab element.

18. The specimen collector of claim 17 wherein said second seal includes a flexible, peripheral skirt portion.

19. The specimen collector of claim 17 and including a third seal mounted within and fixed to said outer tubular member rearwardly of said second seal and having an aperture therein to permit said inner rod to slide therethrough.

20. The specimen collector of claim 19 and including a fourth seal mounted within and fixed to said outer tubular member rearward of said third seal.

21. The specimen collector of claim 20 and including a guiding element attached to a rearward portion of said inner rod.

22. The specimen collector of claim 21 and including gripping means on said inner rod, rearward of said guiding element.

23. The specimen collector of claim 19 and including first and second variable volume chambers between said first and second, and second and third seals, respectively, said second seal permitting passage of fluid between said first and second chambers.

24. The specimen collector of claim 19 wherein said second chamber is prefilled with any one of a culture growth medium, culture transfer medium or biological release agent.

25. The specimen collector of claim 13 wherein said plurality of appendages comprise four substantially identical petal-like elements.

26. The specimen collector of claim 13 wherein said rearward portion of said first seal has an inner diameter larger than radially outermost dimension of said swab element to thereby establish a radial clearance therebetween.

27. The specimen collector of claim 26 wherein said rearward portion is formed with at least one radial protrusion received within an aperture in said outer tubular member, said at least one protrusion having a radial dimension greater than said radial clearance.

28. A specimen collector comprising:
an outer tubular member having a forward end including a forward edge, and a rearward end;
an inner rod slidably received within said outer tubular member and having a non-foamed, molded porous plastic swab element attached to a forward end thereof, and a finger grip attached to a rearward end thereof to thereby enable said swab element to be moved out of and back into the outer tubular member between extended and retracted positions;
a first seal mounted to said forward end of said outer tubular member comprising a forward portion including a plurality of appendages movable between closed and open positions, and a rearward portion received within the forward end of the outer tubular member such that said forward edge of said outer tubular member provides a fulcrum for movement of said appendages from said closed to said open position;
a second seal mounted on said inner rod behind said swab element; and
a third seal mounted within and fixed to said outer tubular member rearwardly of said second seal and having an aperture therein to permit said inner rod to slide therethrough.

29. The specimen collector of claim 28 and including first and second variable volume chambers between said first and second, and second and third seals, respectively, said second seal permitting passage of fluid between said first and second chambers.

30. The specimen collector of claim 29 wherein said second chamber is prefilled with any one of a culture growth medium, culture transfer medium or biological release agent.

31. The specimen collector according to claim 28 and further including a fourth seal mounted within and fixed to said outer tubular member a predetermined distance rearward of said third seal.

32. A specimen collector device comprising:
an outer tubular member having a forward end including a forward edge, and a rearward end;
an inner rod slidably received within said outer tubular member and having a swab element attached to a forward end thereof;
a first seal mounted to said forward end of said outer tubular member comprising a forward portion including a plurality of appendages movable between closed and open positions, and a rearward portion received within the forward end of the outer tubular member such that said forward edge of said outer tubular member provides a fulcrum for movement of said appendages from said closed to said open position.

33. A specimen collector device comprising:
an outer tubular member having a forward end including a forward edge, and a rearward end;
an inner rod slidably received within said outer tubular member and having a swab element attached to a forward end thereof for movement between retracted and extending positions;
a seal mounted to said forward end of said outer tubular member comprising a forward portion including a plurality of appendages movable between closed and open positions, and a rearward portion received within the forward end of the outer tubular member;
wherein said forward portion of said seal is joined to said rearward portion of said seal is joined to said rearward portion at a thickened base portion which provides an abutment surface for engagement with the swab element to thereby open said seal as said swab moves from said retracted to said extended position.

34. The specimen collector of claim 33 wherein said forward edge of said outer tubular member provides a fulcrum for movement of said appendages from said closed to said open position.

* * * * *